(12) United States Patent
Capelli

(10) Patent No.: US 11,794,040 B2
(45) Date of Patent: Oct. 24, 2023

(54) APPARATUSES AND SYSTEMS FOR GENERATING HIGH-FREQUENCY SHOCKWAVES, AND METHODS OF USE

(75) Inventor: Christopher C. Capelli, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/574,228

(22) PCT Filed: Jan. 19, 2011

(86) PCT No.: PCT/US2011/021692
§ 371 (c)(1),
(2), (4) Date: Oct. 22, 2012

(87) PCT Pub. No.: WO2011/091020
PCT Pub. Date: Jul. 28, 2011

(65) Prior Publication Data
US 2013/0046207 A1 Feb. 21, 2013

Related U.S. Application Data

(60) Provisional application No. 61/296,376, filed on Jan. 19, 2010.

(51) Int. Cl.
*A61N 7/00* (2006.01)
*A61B 17/225* (2006.01)

(52) U.S. Cl.
CPC ............. *A61N 7/00* (2013.01); *A61B 17/225* (2013.01); *A61B 2017/2253* (2013.01); *A61N 2007/0034* (2013.01); *A61N 2007/0039* (2013.01)

(58) Field of Classification Search
CPC ............. A61N 7/00; A61N 2007/0034; A61N 2007/0039; A61B 17/22004;
(Continued)

(56) References Cited

U.S. PATENT DOCUMENTS

| 3,364,708 A | 1/1968 | Padberg |
| 3,475,646 A | 10/1969 | Chapman |

(Continued)

FOREIGN PATENT DOCUMENTS

| CN | 1245410 | 2/2000 |
| CN | 101028525 | 9/2007 |

(Continued)

OTHER PUBLICATIONS

Vogel et al., Shock wave emission and cavitation bubble generation by picosecond and nanosecond optical breakdown in water, J. Acoust. Soc. Am. 100 (1) Jul. 1996.*
(Continued)

*Primary Examiner* — Michael T Rozanski
(74) *Attorney, Agent, or Firm* — Mintz, Levin, Cohn, Ferris, Glovsky and Popeo, P.C.

(57) ABSTRACT

Apparatuses and methods for generating therapeutic shock waves. Some embodiments comprise: an acoustic-wave generator configured to emit acoustic waves having at least one frequency between 1 MHz and 1000 MHz; a shock wave housing coupled to the acoustic-wave generator; and a shock wave medium disposed in the shock wave housing; where the apparatus is configured such that if the acoustic-wave generator emits acoustic waves then at least some portion of the acoustic waves will travel through the shock wave medium and form one or more shock waves.

24 Claims, 1 Drawing Sheet

(58) Field of Classification Search
CPC ............... A61B 17/225; A61B 18/26; A61B 2017/2253; A61B 17/2251; A61B 17/2255; A61B 2018/00994; B01F 11/0283
USPC ............................................. 600/439; 601/2
See application file for complete search history.

(56) References Cited

U.S. PATENT DOCUMENTS

| | | | |
|---|---|---|---|
| 3,604,641 A | 9/1971 | Wilson et al. | |
| 3,613,069 A | 10/1971 | Cary | |
| 3,735,764 A | 5/1973 | Balev et al. | |
| 3,769,963 A | 11/1973 | Goldman et al. | |
| 3,942,531 A | 3/1976 | Hoff | |
| 4,005,314 A | 1/1977 | Zinn | |
| 4,311,147 A | 1/1982 | Hausler | |
| 4,715,376 A | 12/1987 | Nowacki et al. | |
| 4,858,597 A | 8/1989 | Kurtze et al. | |
| 4,896,673 A | 1/1990 | Rose et al. | |
| 4,905,671 A | 3/1990 | Senge et al. | |
| 4,928,671 A | 5/1990 | Reichenberger et al. | |
| 4,955,143 A | 9/1990 | Hagelauer | |
| 4,962,752 A | 10/1990 | Reichenberger et al. | |
| 4,979,501 A | 12/1990 | Valchanov et al. | |
| 5,009,232 A | 4/1991 | Hassler et al. | |
| 5,015,929 A | 5/1991 | Cathignol et al. | |
| 5,146,912 A | 9/1992 | Eizenhoefer | |
| 5,149,406 A | 9/1992 | Mullen et al. | |
| 5,150,713 A | 9/1992 | Okazaki | |
| 5,193,527 A | 3/1993 | Schafer | |
| 5,195,508 A | 3/1993 | Muller et al. | |
| 5,204,820 A | 4/1993 | Strobel et al. | |
| 5,231,976 A | 8/1993 | Wiksell | |
| 5,240,005 A * | 8/1993 | Viebach | 601/2 |
| 5,245,988 A | 9/1993 | Einars et al. | |
| 5,259,368 A | 11/1993 | Wiksell | |
| 5,284,143 A | 2/1994 | Rattner | |
| 5,304,170 A | 4/1994 | Green | |
| 5,304,207 A | 4/1994 | Stromer | |
| 5,327,890 A | 7/1994 | Matura et al. | |
| 5,360,447 A | 11/1994 | Koop | |
| 5,374,236 A | 12/1994 | Hassler | |
| 5,393,296 A | 2/1995 | Rattner | |
| 5,409,446 A | 4/1995 | Rattner | |
| 5,419,327 A | 5/1995 | Rohwedder et al. | |
| 5,423,803 A | 6/1995 | Tankovich et al. | |
| 5,435,304 A | 7/1995 | Oppelt et al. | |
| 5,458,652 A | 10/1995 | Uebelacker | |
| 5,509,200 A | 4/1996 | Frankeny et al. | |
| 5,529,572 A | 6/1996 | Spector | |
| 5,595,178 A | 1/1997 | Voss et al. | |
| 5,618,275 A | 4/1997 | Bock | |
| 5,658,239 A * | 8/1997 | Delmenico | 601/4 |
| 5,675,495 A | 10/1997 | Biermann et al. | |
| 5,676,159 A * | 10/1997 | Navis | 128/846 |
| 5,709,676 A | 1/1998 | Alt | |
| 5,722,411 A | 3/1998 | Suzuki et al. | |
| 5,737,462 A | 4/1998 | Whitehouse et al. | |
| 5,790,305 A | 8/1998 | Marcellin-Dibon et al. | |
| 5,827,204 A | 10/1998 | Grandia et al. | |
| 6,013,122 A | 1/2000 | Klitzman et al. | |
| 6,036,661 A | 3/2000 | Schwarze et al. | |
| 6,039,694 A * | 3/2000 | Larson | A61B 8/4281 600/459 |
| 6,058,932 A | 5/2000 | Hughes | |
| 6,080,119 A | 6/2000 | Schwarze et al. | |
| 6,096,029 A | 8/2000 | O'Donnell, Jr. | |
| 6,113,559 A | 9/2000 | Klopotek | |
| 6,113,560 A | 9/2000 | Simnacher | |
| 6,123,679 A | 9/2000 | Lafaut et al. | |
| 6,176,839 B1 | 1/2001 | Deluis et al. | |
| 6,186,963 B1 | 2/2001 | Schwarze et al. | |
| 6,210,329 B1 * | 4/2001 | Christmas | A61B 19/0248 600/437 |
| 6,217,531 B1 | 4/2001 | Reitmajer | |
| 6,309,355 B1 | 10/2001 | Cain et al. | |
| 6,325,769 B1 * | 12/2001 | Klopotek | 601/2 |
| 6,350,245 B1 | 2/2002 | Cimino | |
| 6,368,929 B1 | 4/2002 | Hill et al. | |
| 6,390,995 B1 | 5/2002 | Ogden et al. | |
| 6,450,979 B1 | 9/2002 | Miwa et al. | |
| 6,454,713 B1 | 9/2002 | Ishibashi et al. | |
| 6,487,447 B1 | 11/2002 | Weimann et al. | |
| 6,491,685 B2 | 12/2002 | Visuri | |
| 6,500,141 B1 | 12/2002 | Irion et al. | |
| 6,515,842 B1 | 2/2003 | Hayworth et al. | |
| 6,519,376 B2 | 2/2003 | Biagi et al. | |
| 6,551,308 B1 | 4/2003 | Muller et al. | |
| 6,666,834 B2 | 12/2003 | Restle et al. | |
| 6,755,821 B1 | 6/2004 | Fry | |
| 6,800,122 B2 | 10/2004 | Anderson et al. | |
| 6,905,467 B2 | 6/2005 | Bradley | |
| 6,942,663 B2 | 9/2005 | Vargas et al. | |
| 6,948,843 B2 | 9/2005 | Laugharn et al. | |
| 6,972,116 B2 | 12/2005 | Brill et al. | |
| 7,189,209 B1 | 3/2007 | Ogden et al. | |
| 7,250,047 B2 | 7/2007 | Anderson et al. | |
| 7,311,678 B2 | 12/2007 | Spector | |
| 7,364,554 B2 | 4/2008 | Bolze et al. | |
| 7,405,510 B2 | 6/2008 | Kaminski et al. | |
| 7,470,240 B2 | 12/2008 | Schultheiss et al. | |
| 7,507,213 B2 | 3/2009 | Schultheiss et al. | |
| 7,588,547 B2 | 9/2009 | Deem et al. | |
| 7,867,178 B2 | 1/2011 | Simnacher | |
| 7,985,189 B1 | 7/2011 | Ogden et al. | |
| 7,988,631 B2 | 8/2011 | Bohris | |
| 8,057,408 B2 | 11/2011 | Cain et al. | |
| 8,088,073 B2 | 1/2012 | Simnacher et al. | |
| 8,092,401 B2 | 1/2012 | Schultheiss | |
| 8,102,734 B2 | 1/2012 | Sliwa et al. | |
| 8,235,899 B2 | 8/2012 | Hashiba | |
| 8,257,282 B2 | 9/2012 | Uebelacker et al. | |
| 8,298,162 B2 | 10/2012 | Del Giglio | |
| 8,323,220 B2 | 12/2012 | Babaev | |
| 8,343,420 B2 | 1/2013 | Cioanta et al. | |
| 8,357,095 B2 | 1/2013 | Anderson et al. | |
| 8,672,721 B2 | 3/2014 | Camilli | |
| 8,684,970 B1 | 4/2014 | Koyfman | |
| 2002/0009015 A1 * | 1/2002 | Laugharn et al. | 366/108 |
| 2002/0193831 A1 | 12/2002 | Smith | |
| 2003/0167964 A1 | 9/2003 | Anderson et al. | |
| 2003/0233045 A1 * | 12/2003 | Vaezy | A61B 8/4281 600/437 |
| 2004/0006288 A1 | 1/2004 | Spector et al. | |
| 2004/0181219 A1 | 9/2004 | Goble et al. | |
| 2005/0015023 A1 * | 1/2005 | Ein-Gal | A61B 17/22004 601/2 |
| 2005/0150830 A1 * | 7/2005 | Laugharn | B01F 11/02 210/634 |
| 2006/0036168 A1 | 2/2006 | Liang et al. | |
| 2006/0064082 A1 | 3/2006 | Bonutti | |
| 2006/0158956 A1 | 7/2006 | Laugharn et al. | |
| 2006/0173388 A1 | 8/2006 | Ginter et al. | |
| 2006/0184071 A1 | 8/2006 | Klopotek | |
| 2006/0200116 A1 | 9/2006 | Ferren et al. | |
| 2006/0211958 A1 | 9/2006 | Rosenberg et al. | |
| 2007/0016112 A1 | 1/2007 | Schultheiss et al. | |
| 2007/0038060 A1 | 2/2007 | Cerwin et al. | |
| 2007/0049829 A1 | 3/2007 | Kaminski et al. | |
| 2007/0055180 A1 | 3/2007 | Deem et al. | |
| 2007/0065420 A1 * | 3/2007 | Johnson | A61N 7/02 424/93.7 |
| 2007/0135755 A1 | 6/2007 | Bernabei et al. | |
| 2007/0198068 A1 | 8/2007 | Chan et al. | |
| 2007/0219760 A1 | 9/2007 | Yang et al. | |
| 2007/0239072 A1 | 10/2007 | Shultheiss et al. | |
| 2007/0239082 A1 | 10/2007 | Schultheiss et al. | |
| 2007/0239084 A1 | 10/2007 | Voss | |
| 2007/0249939 A1 | 10/2007 | Gerbi et al. | |
| 2008/0009774 A1 | 1/2008 | Capelli et al. | |
| 2008/0009885 A1 | 1/2008 | Del Giglio | |
| 2008/0021447 A1 | 1/2008 | Davison et al. | |
| 2008/0071198 A1 | 3/2008 | Ogden et al. | |
| 2008/0107744 A1 | 5/2008 | Chu | |

(56) References Cited

U.S. PATENT DOCUMENTS

| | | |
|---|---|---|
| 2008/0132810 A1 | 6/2008 | Scoseria et al. |
| 2008/0146971 A1* | 6/2008 | Uebelacker et al. ............ 601/4 |
| 2008/0154157 A1 | 6/2008 | Altshuler et al. |
| 2008/0183200 A1* | 7/2008 | Babaev ........................ 606/169 |
| 2008/0194967 A1 | 8/2008 | Sliwa et al. |
| 2008/0195003 A1 | 8/2008 | Sliwa et al. |
| 2008/0262483 A1* | 10/2008 | Capelli .................... A61N 7/02 606/9 |
| 2008/0269163 A1* | 10/2008 | Sostaric ............ A61K 31/7004 514/53 |
| 2008/0269608 A1 | 10/2008 | Anderson et al. |
| 2008/0319356 A1 | 12/2008 | Cain et al. |
| 2009/0018472 A1 | 1/2009 | Soltani et al. |
| 2009/0062644 A1 | 3/2009 | McMorrow et al. |
| 2009/0275832 A1* | 11/2009 | Gelbart .................... A61B 8/08 600/439 |
| 2010/0049098 A1 | 2/2010 | Shalgi et al. |
| 2010/0076349 A1 | 3/2010 | Babaev |
| 2010/0082019 A1 | 4/2010 | Neev |
| 2010/0087899 A1 | 4/2010 | Erez et al. |
| 2010/0168575 A1 | 7/2010 | Hashiba |
| 2010/0204617 A1* | 8/2010 | Ben-Ezra ......................... 601/2 |
| 2010/0208467 A1 | 8/2010 | Dross |
| 2010/0249768 A1 | 9/2010 | Avramenko et al. |
| 2010/0274161 A1 | 10/2010 | Azhari et al. |
| 2010/0280420 A1 | 11/2010 | Barthe et al. |
| 2010/0331741 A9 | 12/2010 | Cioanta et al. |
| 2011/0034832 A1 | 2/2011 | Cioanta et al. |
| 2011/0087157 A1 | 4/2011 | Cioanta et al. |
| 2012/0157892 A1 | 6/2012 | Reitmajer et al. |
| 2012/0167174 A1 | 6/2012 | Saxena et al. |
| 2012/0253240 A1 | 10/2012 | Uebelacker et al. |
| 2012/0253416 A1 | 10/2012 | Erez et al. |
| 2012/0310232 A1 | 12/2012 | Erez |
| 2012/0323147 A1 | 12/2012 | Scheirer |
| 2012/0330288 A1 | 12/2012 | Clementi et al. |
| 2013/0018287 A1* | 1/2013 | Capelli .................... A61N 7/00 601/2 |
| 2013/0046179 A1 | 2/2013 | Humayun |
| 2013/0046207 A1 | 2/2013 | Capelli |
| 2013/0345600 A1 | 12/2013 | Katragadda et al. |
| 2014/0005576 A1 | 1/2014 | Adams et al. |
| 2014/0094718 A1 | 4/2014 | Feldman |
| 2014/0228820 A1 | 8/2014 | Blaskowski et al. |
| 2014/0243715 A1 | 8/2014 | Cioanta et al. |
| 2014/0243847 A1 | 8/2014 | Hakala et al. |
| 2014/0257144 A1 | 9/2014 | Capelli et al. |
| 2014/0276693 A1 | 9/2014 | Altshuler et al. |
| 2014/0276722 A1 | 9/2014 | Parihar et al. |
| 2014/0277219 A1 | 9/2014 | Nanda |
| 2014/0378740 A1 | 12/2014 | Wagner et al. |
| 2015/0105702 A1 | 4/2015 | Wagner et al. |
| 2015/0126913 A1 | 5/2015 | Jurna et al. |
| 2015/0217111 A1 | 8/2015 | Stevenson et al. |
| 2016/0016013 A1 | 1/2016 | Capelli et al. |
| 2016/0067139 A1 | 3/2016 | Katragadda et al. |
| 2016/0166837 A1 | 6/2016 | Strommer et al. |
| 2016/0262778 A1 | 9/2016 | Du |
| 2016/0271419 A1 | 9/2016 | Varghese et al. |
| 2018/0116905 A1 | 5/2018 | Capelli et al. |
| 2018/0221688 A1 | 8/2018 | Cioanta et al. |

FOREIGN PATENT DOCUMENTS

| | | |
|---|---|---|
| CN | 101146574 | 3/2008 |
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| FR | 2605874 | 5/1988 |
| GB | 2303552 | 2/1997 |
| JP | 53-111689 | 9/1978 |
| JP | S61-293447 | 12/1986 |
| JP | S 61-293447 | 12/1986 |
| JP | 62-192150 | 8/1987 |
| JP | S 63-023775 | 2/1988 |
| JP | S63-183050 | 7/1988 |
| JP | S 63-183050 | 7/1988 |
| JP | H05-207593 A | 8/1993 |
| JP | 6-7365 | 1/1994 |
| JP | H 06-505648 | 6/1994 |
| JP | H06-505648 | 6/1994 |
| JP | 8-140984 | 6/1996 |
| JP | 08140984 A * | 6/1996 |
| JP | H 08140984 | 6/1996 |
| JP | 8-194079 | 7/1996 |
| JP | 1996-222472 | 8/1996 |
| JP | H0-8224253 | 9/1996 |
| JP | 9-103434 | 4/1997 |
| JP | H09103434 | 4/1997 |
| JP | H 10192289 | 7/1998 |
| JP | H 10328192 | 12/1998 |
| JP | 2003-500126 | 1/2003 |
| JP | 2004526507 | 9/2004 |
| JP | 2005514142 | 5/2005 |
| JP | 2007-000218 | 1/2007 |
| JP | 2009506870 | 2/2009 |
| JP | 2009-518126 | 4/2009 |
| JP | 2009-527262 | 7/2009 |
| JP | 2009543614 | 12/2009 |
| JP | 2012-516170 | 7/2012 |
| JP | 2013537559 | 10/2013 |
| JP | 2014-507990 | 4/2014 |
| JP | 2014525782 | 10/2014 |
| JP | 2016/523602 | 8/2016 |
| JP | 2017-500078 | 1/2017 |
| JP | 61-73644 | 8/2017 |
| KR | 101886863 | 8/2018 |
| RU | 2121812 | 11/1998 |
| RU | 2121812 C1 | 11/1998 |
| RU | 2151559 | 6/2000 |
| RU | 2151559 C1 | 6/2000 |
| TW | 200604017 | 2/2006 |
| TW | I 292341 | 1/2008 |
| TW | I 350249 | 10/2011 |
| WO | WO 91/10227 | 7/1991 |
| WO | WO 2000/071207 | 11/2000 |
| WO | WO 2002/030256 | 4/2002 |
| WO | WO 2004/080147 | 9/2004 |
| WO | WO 2007/067563 | 6/2007 |
| WO | WO 2007/088546 | 8/2007 |
| WO | WO/07 /146988 | 12/2007 |
| WO | WO 2007/146988 | 12/2007 |
| WO | WO 2008/052198 | 5/2008 |
| WO | WO 2008/074005 | 6/2008 |
| WO | WO 2008/137942 | 11/2008 |
| WO | WO 2010/086301 | 8/2010 |
| WO | WO 2011/077466 | 6/2011 |
| WO | WO/11/091020 | 7/2011 |
| WO | WO 2011/091020 | 7/2011 |
| WO | WO 2012/107830 | 8/2012 |
| WO | WO 2013/012724 | 1/2013 |
| WO | WO 2010/122517 | 8/2014 |
| WO | WO 2014/138582 | 9/2014 |
| WO | WO 2014/191263 | 12/2014 |
| WO | WO 2015/176001 | 11/2015 |
| WO | WO 2017/165595 | 9/2017 |
| WO | WO 2018/136514 | 7/2018 |

(56) References Cited

OTHER PUBLICATIONS

Fernando, A Nonlinear Computational Method for the Propagation of Shock Waves in Aero-engine Inlets Towards a new Model for Buzz-saw Noise Prediction. 15th AIAA/CEAS Aeroacoustics Conference (30th AIAA Aeroacoustics Conference) May 11-13, 2009, p. 1-18.*

Reichenberger, Electromagnetic Acoustic Source for Extracorporeal Geneartion of Shock Waves in Lithotripsy, Siemens Forsch, 1986, 187-194.*

Falco, "Single-point Nonlinearity Indicators for the Propagation of High-amplitude Acoustic Signals," Ph.D. Thesis, Graduate Program in Acoustics, , The Pennsylvania State University, University Park, PA, May 2007.*

International Search Report and Written Opinion issued for PCT/US2011/021692, dated Sep. 20, 2011, 10 pages.

Sheth and Pandya, "Melsama: A comprehensive update (Part I)", *Journal of the American Academy of Dermatology*, 65:689-697, 2011.

International Preliminary Report on Patentability of PCT/US2011/021692, dated Jul. 24, 2012, 6 pages.

Search Report and Written Opinion in PCT/US12/46674 dated Oct. 26, 2012.

Solis el al., "Experimental Nonsurgical Tattoo Removal in a Guinea Pig Model with Topical Imiquimod and Tretinoin", Dermatol Surg. 2002, 28:83-87.

Wolfrum el al., "Shock wave induced interaction of microbubbles and boundaries", Physics of Fluids, vol. 15, No. 10, Oct. 2003, pp. 2916-2922.

International Search Report and Written Opinion issued in PCT/US2011/021692, dated Sep. 20, 2011.

International Search Report and Written Opinion issued in PCT/US2012/046674, dated Oct. 26, 2012.

Patent Examination Report No. 2 in Australian Patent Application No. 2011207601 dated Apr. 8, 2014.

Office Action issued in Corresponding European Patent Application No. 11735097.5, dated Nov. 15, 2018.

Office Action Issued in Corresponding Korean Patent Application No. 10-2014-7003927, dated Dec. 26, 2018.

Baumler et al., Q-Switch Laser and Tattoo Pigments: First Results of the Chemical and Photophysical Analysis of 41 Compounds, Lasers in Surgery and medicine 26:13-21 (2000), pp. 13-21.

Bickle, Abdominal X Rays Made Easy: Calcification, Student BMJ vol. 10, Aug. 2002, 272-274.

Burov, et al., "Nonlinear Ultrasound: Breakdown of Microscopic Biological Structures and Nonthermal Impact on Malignant Tumor," *Doklady Biochemistry and Biophysics*, 383(3), pp. 101-104. (2002).

Chen et al., "The disappearance of ultrasound contrast bubbles: Observations of bubble dissolution and Cavitation nucleation", Ultrasound in Med. & Biol., vol. 28, No. 6, pp. 793-803, 2002.

Decision on Grant Patent for Invention in Russian Application No. 2012135506/14(057136) dated May 12, 2014.

Delius, et al., "Biological Effects of Shock Waves: Kidney Haemorrhage by Shock Waves in Dogs—Administration Rate Dependence," *Ultrasound Med Biol.*, 14(8), 689-694, 1988.

Eisenmenger, W. et al., "The First Clinical Results of Wide-Focus and Low-Pressure ESWL" Ultrasound in Med. & Biol., vol. 28, No. 6, pp. 769-774, 2002.

Eisenmenger, Wolfgang, "The Mechanisms of Stone Fragmentation in ESWL", Ultrasound in Med. & Biol., vol. 27, No. 5, pp. 683-693, 2001.

Examination Reporting Issued in Australian Patent Application No. 2016277677, dated Dec. 11, 2017.

Extended European Search Report in European Application No. 12814465.6 dated Feb. 24, 2015.

Fernando, "A Nonlinear Computational Method for the Propagation of Shock Waves in Aero-Engine Inlets Towards A New Model for Buzz-Saw Noise Prediction," 15th AIAA/CEAS Aeroacoustics Conference (30th Aerocoustics Conference) May 11-13, 2009, 1-18.

Gillitzer, et al., "Low-Frequency Extracorporeal Shock Wave Lithotripsy Improves Renal Pelvic Stone Disintegration An A Pig Model," *BJU Int*, 176, 1284-1288, 2009.

Ho et al., "Laser-Tattoo Removal—A Study of the Mechanism and the Optimal Treatment Strategy via Computer Simulations", Lasers in Surgery and medicine 30:389-391 (2002).

International Preliminary Report on Patentability of PCT/US2011/021692, dated Jul. 24, 2012.

International Search Report and Written Opinion In PCT/US2012/046674 dated Oct. 26, 2012.

International Search Report and Written Opinion Issued for PCT/US2011/021692, dated Sep. 20, 2011.

Kuhn et al., "Impact of extracorporeal shock waves on the human skin with cellulite: A case study of an unique instance", Clinical Interventions of Aging, 3(1):201-210, 2008.

Kuperman-Beade et al., "Laser Removal of Tattoos", Am J Clin Dermatol 2001: 2(1):21-25.

Kuzmin et al., "Ultrasonic Cavitational Chemical Technologies", XI Session of the Russian Acoustical Society, Moscow, Nov. 19-23, 2001.

Liu, et al., "Optimized Design of LED Freeform Lens For Uniform Circular Illumination," *Journal of Zhejiang University-Science C*, Computer & Electron, 13(12), 929-936, 2012.

Madbouly, et al., "Slow Versus Fast Shock Wave Lithotripsy Rate for Urolithiasis: A Prospective Randomized Study," *The Journal of Urology*, 173, 127-130, 2005.

Nana, et al., "Application of the Multiple Low-Energy Q-Switched Laser for the Treatment of Tattoos in 21 Cases," China Aesthetic Medicine, 4(21), 621-622, 2012. (English Abstract).

Ng et al., "Therapeutic Ultrasound: Its Application in Drug Delivery", Medicinal Research Reviews, vol. 22, No. 2, 204-223, 2002.

Notice of Allowance in Canadian Application No. 2,787,528 dated Apr. 9, 2014.

Notice of Final Rejection in Korean Application No. 10-2012-7021437 dated Jun. 26, 2014.

Notice of Preliminary Rejection in Korean Application No. 10-2012-7021437 dated Oct. 24, 2013.

Office Action Issued in Corresponding Japanese Patent Application No. 2017-133546 with English Translation, dated Jun. 4, 2018.

Office Action in Chinese Patent Application No. 201180011442.0 dated Mar. 2, 2015.

Office Action in Chinese Patent Application No. 201280041817.2 dated Feb. 4, 2015.

Office Action in Japanese Patent Application No. 2012-550085 dated Jun. 10, 2015.

Office Action in Japanese Patent Application No. 2012-550085 dated Oct. 2, 2014.

Office Action Issued in Corresponding Australian Patent Application No. 2019200537, dated Mar. 3, 2020.

Office Action issued in Corresponding European Application No. 11735097.5, dated Nov. 15, 2018.

Office Action Issued in Corresponding Indian Patent Application No. 334/DELNP/2014, dated Jan. 29, 2020.

Office Action Issued in Corresponding Korean Application No. 10-2014-7003927, dated Dec. 26, 2018.

Office Communication in Chinese Application No. 201180011442.0 dated Jul. 3, 2014.

Office Communication in Chinese Patent Application No. 201180011442.0 dated Jul. 3, 2014.

Ogden et al., Principles of Shock Wave Therapy, Clinical Orthopaedics and Related Research, No. 387, pp. 8-17.

Patent Examination Report No. 1 in Australian Patent Application No. 2012284323 dated Jan. 9, 2014.

Patent Examination Report No. 2 in Australian Patent Application No. 2011207601 dated Apr. 4, 2014.

Reichenberger, "Electromagnetic Acoustic Source for Extracorporeal Generation of Shock Waves in Lithotripsy," Siemens Forsch, 1986, 187-194.

Ross et al., "Comparison of Responses of Tattoos to Picosecond and Nanosecond Q-Switched Neodymium: YAG Lasers" ARCH Dermatol/vol. 134, Feb. 1998, pp. 167-171.

(56) References Cited

OTHER PUBLICATIONS

Sheth and Pandya, "Melsama: A comprehensive update (Part 1)", *Journal of the American Academy of Dermatology*, 65:689-697, 2011.

Sheth and Pandya, "Melsama: A comprehensive update (Part II)", *Journal of the American Academy of Dermatology*, 65:699-714, 2011.

Solis et al., "Experimental Nonsurgical Tattoo Removal in a Guinea Pig Model with Topical Imiquimod and Tretinoin", Dermatol Surg. 2002, 28:83-87.

Timko et al., "In Vitro Quantitative Chemical Analysis of Tattoo Pigments", ARCH Dermatol/vol. 137, Feb. 2001, pp. 143-147.

Varma, S., "Tattoo Ink Darkening of a yellow Tattoo after Q-Switched Laser Treatment", 2002 Blackwell Science Ltd., Clinical and Experimental Dermatology, 27, 461-463.

Wolfrum et al., "Shock wave induced interaction of microbubbles and boundaries", Physics of Fluids, vol. 15, No. 10, Oct. 2003, pp. 2916-2922.

Boxman, et al., "Handbook of Vacuum Arc Science and Technology: Fundamentals and Applications," Park Ridge, New Jersey: Noyes Publications, pp. 316-319, 1995.

Extended European Search Report Issued in Corresponding European Patent Application No. 20153807.1, dated Jun. 9, 2020.

International Preliminary Report on Patentability Issued in Corresponding PCT Application No. PCT/US2017/042122, dated Jan. 22, 2019.

International Search Report and Written Opinion Issued in Corresponding PCT Application No. PCT/US2017/042122, dated Jan. 9, 2018.

International Search Report and Written Opinion Issued in Corresponding PCT Application No. PCT/US14/21746, dated Sep. 12, 2014.

Office Action Issued in Corresponding Japanese Patent Application No. 2019-012062, dated Jun. 16, 2020.

Partial Supplementary Search Report Issued in Corresponding European Patent Application No. EP18754679.1, dated Jul. 29, 2020.

Schmitz, et al., "Treatment of Chronic Plantar Fasciopathy with Extracorporeal Shock Waves (Review)," *Journal of Orthopaedic Surgery and Research*, 8(1); 31, 2013.

Ushakov, et al., "Impulse Breakdown of Liquids," New York, New York: Springer. 2007.

Office Action Issued in Chinese Patent Application No. 201910058064, dated Feb. 8, 2021.

Office Action Issued in Chinese Patent Application No. 201910058064, dated Oct. 25, 2021.

Teng, J., "Ultrasound: an alternative solution for removing tattoos." *Massachusetts Institute of Technology*, pp. 3-6, 12-65; 2005.

Office Action issued in Australian Patent Application No. 2021201670, dated Jun. 20, 2022.

Office Action issued in U.S. Appl. No. 16/478,611, dated Jun. 30, 2022.

Troilius, "Effective Treatment of traumatic Tattoos with a Q-switched Nd:YAG laser," Lasers Surg. Med., 22:103-108, 1998.

International Search Report and Written Opinion Issued in Corresponding PCT Application No. PCT/US2020/026425 dated Sep. 2, 2020.

Office Action and Search Report issued in Corresponding Chinese Application No. 201780056472.0, dated Jan. 19, 2022 (English Translation provided).

Official Action issued in Japanese Patent Application No. 2019-544631, dated Sep. 16, 2022.

Official Action issued in U.S. Appl. No. 16/486,920, dated Sep. 14, 2022.

Carlberg, "Upgrading from Stepper to Servo," Yaskawa America Inc., pp. 1-7, 2011.

English translation of Office Action issued in Japanese Patent Application No. 2021-184610, dated Nov. 18, 2022.

Manousakas et al., "Development of a system of automatic gap-adjusted electrodes for shock wave generators," Review of Scientific Instruments, 75(11):4811-4819, 2004.

Office Action issued in U.S. Appl. No. 16/478,611, dated Oct. 31, 2022.

Office Action issued in Australian Patent Application No. 2018221251, dated Nov. 10, 2022.

English translation of Office Action issued in Korean Patent Application No. 10-2019-7005043 dated Sep. 28, 2022.

Office Action issued in U.S. Appl. No. 16/087,976 dated Oct. 13, 2022.

Notice of Allowance issued in U.S. Appl. No. 17/648,790, dated Feb. 28, 2023.

Office Communication issued in Japanese Patent Application No. 2018-550349, dated Mar. 7, 2023. (English translation).

Office Communication issued in U.S. Appl. No. 16/904,125, dated Mar. 23, 2023.

Office Communication issued in U.S. Appl. No. 17/096,932, dated Mar. 28, 2023.

Office Communication issued in U.S. Appl. No. 16/319,509, dated Apr. 10, 2023.

\* cited by examiner

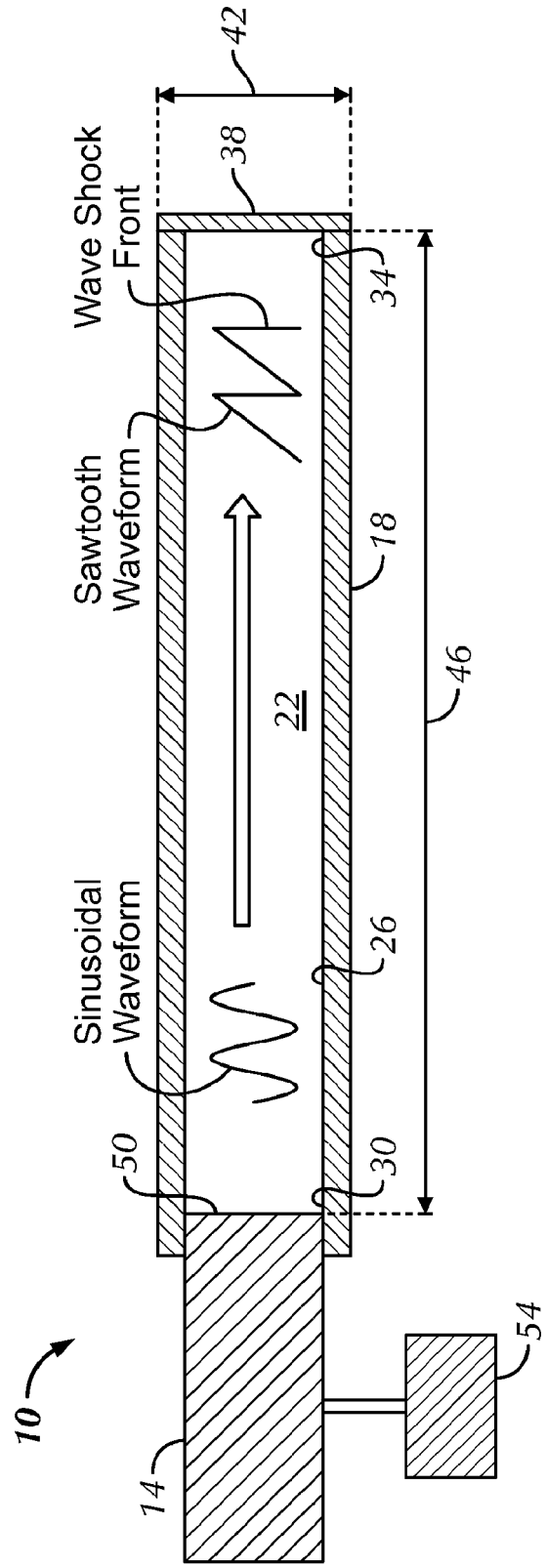

APPARATUSES AND SYSTEMS FOR GENERATING HIGH-FREQUENCY SHOCKWAVES, AND METHODS OF USE

RELATED APPLICATION

This application is a National Phase Application of International Application No. PCT/US2011/021692, which claims priority to U.S. Provisional Patent Application No. 61/296,376, filed Jan. 19, 2010, the disclosures of which are incorporated here in their entirety.

BACKGROUND

1. Field of the Invention

The present invention relates generally to therapeutic uses for shock waves. More particularly, but not by way of limitation, the present invention relates to an apparatus for generating therapeutic shock waves (shock waves with therapeutic uses).

2. Background Information

Shockwaves may be used in certain medical and aesthetic therapies. Since the early 1980s, shockwaves have been used in the form of extracorporeal lithotripsy, in which pulses may be used to form shock fronts for fragmentation of renal calculi. The shockwave source in lithotripsy is typically generated by the discharge of electric energy between test electrodes.

More recently, shockwaves have been described for use in medical therapy in which the shockwaves may not originate from the discharge of electric energy between test electrodes. For example, U.S. Pat. No. 6,325,769, by Peter J. Klopotek, describes a method and apparatus for reducing skin wrinkles, comprising applying a focused ultrasound beam to a region of human skin to generate a shockwave to mechanically disrupt a dermis layer in the region of the skin so as to cause a change in the dermis layer of the skin that results in a change in a smoothness of the epidermis layer of the skin. Klopotek discloses that the acoustic pulses used to treat the skin have pressure amplitudes that are sufficiently high to introduce nonlinearity. The result of this nonlinearity is distortion of the waveform of the pulses as they travel through the skin. These waveforms convert from a typical Gaussian amplitude (pressure) profile to a waveform having a much sharper leading face. Klopotek claims that the waveform was "essentially a 'shock-wave' in the target region below the surface of the skin." Klopotek further states that in a normal wave propagation mode, there is essentially no movement of dermal material. However, when acoustic waves exhibit nonlinearity, the dermal tissue moves, creating a negative pressure, or vacuum effect, in the tissue in the wake of the pulse—which can induce tissue damage, tearing tissue structures apart, heating the region and, thereby, triggering the synthesis of new connected tissue.

A problem with the generation of shockwaves as described by Klopotek is that it is not predictable. As described by Klopotek, the shockwaves form as they travel through the skin because of the nonlinear nature of the skin tissue. The formation of a shockwave is dependent on the frequency and amplitude of the acoustic waves. Additionally, the formation of a shockwave is dependent on the medium in which the wave is traveling. Depending on the frequency, amplitude and media, the distance at which a shockwave forms from the transducer head is relatively large and can vary drastically depending on the type of tissue. As a result, up to now, due to variations in the nonlinearity of the tissue that is being treated, creating consistent high-frequency shockwaves suitable for therapy is difficult.

SUMMARY

The present disclosure includes embodiments of apparatuses and methods for generating therapeutic shock waves.

Some embodiments of the present apparatuses for generating therapeutic shock waves, comprise: an acoustic-wave generator configured to emit acoustic waves having at least one frequency between 1 MHz and 1000 MHz; a shockwave housing coupled to the acoustic-wave generator; and a shockwave medium disposed in the shockwave housing; where the apparatus is configured such that if the acoustic-wave generator emits acoustic waves then at least some portion of the acoustic waves will travel through the shockwave medium and form one or more shock waves. In some embodiments, the shockwave medium is unitary with the shockwave housing. In some embodiments, the shockwave housing and shockwave medium comprise silicone. In some embodiments, the shockwave medium comprises one or more bubbles. In some embodiments, the shockwave housing defines a chamber, and where the shockwave medium is disposed in the chamber. In some embodiments, the shockwave medium comprises a fluid. In some embodiments, the shockwave medium comprises a gel. In some embodiments, the shockwave medium comprises a liquid.

In some embodiments, the shockwave medium is configured such that in the presence of acoustic waves from the acoustic-wave generator the shockwave medium will exhibit nonlinear properties. In some embodiments, the shockwave medium comprises one or more of: bubbles, solid particles, or a combination of bubbles and solid particles. In some embodiments, the shockwave medium comprises one or more of: water, glycerin, poly(ethylene glycol) (PEG), propylene glycol, silicone oil, alcohol, or a combination of two or more of these.

In some embodiments, the shockwave housing defines a chamber having an inlet end coupled to the acoustic-wave generator and an outlet end extending from the acoustic-wave generator, and where the shockwave housing includes an end cap covering the outlet end of the chamber. In some embodiments, the chamber has a circular cross-sectional shape. In some embodiments, the chamber has a rectangular cross-sectional shape. In some embodiments, the chamber has a square cross-sectional shape. In some embodiments, the chamber has a ovular cross-sectional shape. In some embodiments, the chamber has a triangular cross-sectional shape. In some embodiments, the end cap is configured to permit shockwaves to exit the outlet end of the shockwave chamber. In some embodiments, the end cap is configured such that attenuation of a shockwave exiting the end cap will be less than twenty percent. In some embodiments, the end cap comprises at least one of: polymer, hydrogel, plastic, or silicone. In some embodiments, the inlet end of the chamber has a transverse internal dimension at least as large as a corresponding transverse external dimension of the acoustic-wave generator. In some embodiments, the chamber has a substantially constant cross-section between the inlet end and the outlet end. In some embodiments, the chamber has a varying cross-section between the inlet end and the outlet end.

In some embodiments, the shockwave housing is configured such that if acoustic waves are incident on the shockwave housing from within the shockwave chamber, then the shockwave housing will reflect at least some portion of the incident acoustic waves back into the shockwave chamber. In some embodiments, the distance from the acoustic-wave generator to the outlet end of the chamber is between 100 and 1000 percent of at least one internal transverse dimension of the chamber. In some embodiments, the distance from the acoustic-wave generator to the outlet end of the chamber is between 100 and 1000 percent of the minimum internal transverse dimension of the chamber. In some embodiments, the distance from the acoustic-wave generator to the outlet end of the chamber is between 300 and 900 percent of at least one internal transverse dimension of the chamber. In some embodiments, the distance from the acoustic-wave generator to the outlet end of the chamber is between 400 and 800 percent of at least one internal transverse dimension of the chamber.

In some embodiments, the distance from the acoustic-wave generator to the outlet end of the chamber is greater than or equal to:

$$L = \frac{c_0^3 \rho_0}{\epsilon \omega P_0} = \frac{\lambda}{2\pi M_\omega}$$

where $\mathcal{E}$ =nonlinear parameter of shockwave medium; $\omega$=frequency of acoustic wave; $\rho_0$=density of the shockwave medium; $\lambda$=wavelength of acoustic wave; $c_0$=velocity of sound in the shockwave medium; $P_0$=pressure amplitude in shockwave medium; and $M_\omega$=acoustic mach number=$P_0 \div (c_0^2 \rho_0)$.

In some embodiments, the acoustic-wave generator comprises an ultrasound head. In some embodiments, the acoustic-wave generator comprises ceramic. In some embodiments, the acoustic-wave generator comprises a piezoelectric acoustic element.

Some embodiments further comprise: a controller coupled to the acoustic-wave generator and configured to actuate the acoustic-wave generator to emit acoustic waves. In some embodiments, the controller is configured to adjust the acoustic-wave generator to vary at least one of the amplitude and frequency of acoustic waves emitted from the acoustic-wave generator. In some embodiments, the controller is configured to actuate the acoustic-wave generator to continuously emit acoustic waves for a period of time. In some embodiments, the controller is configured to actuate the acoustic-wave generator to emit acoustic waves in an intermittent on-off sequence. In some embodiments, the controller is configured to actuate the acoustic-wave generator to emit acoustic waves in a periodic on-off sequence.

In some embodiments, the acoustic-wave generator is a first acoustic-wave generator, and the apparatus further comprises: a second acoustic-wave generator configured to emit acoustic waves having at least one frequency between 1 MHz and 1000 MHz; where the shockwave housing is also coupled to the second acoustic-wave generator; where the apparatus is configured such that if the second acoustic-wave generator emits acoustic waves then at least some portion of the acoustic waves will travel through the shockwave medium and form one or more shock waves; and where the controller is also coupled to the second acoustic-wave generator and configured to actuate second the acoustic-wave generator to emit acoustic waves. In some embodiments, the controller is configured to actuate the first and second acoustic-wave generators such that the acoustic waves that are emitted from the second acoustic-wave generator are out-of-phase from the waves that are emitted from the first acoustic-wave generator.

In some embodiments, the apparatus is configured to generate shock waves having an intensity between 50 and 1000 Watts per square centimeter (W/cm$^2$). In some embodiments, the apparatus is configured to generate shock waves having an intensity between 100 and 500 W/cm$^2$. In some embodiments, the apparatus is configured to generate 100 or more shockwaves per minute. In some embodiments, the apparatus is configured to generate 500 or more shock waves per minute. In some embodiments, the apparatus is configured to generate 1000 or more shock waves per minute.

In some embodiments, the apparatus is configured to fit within a box having a length of 3 feet, a width of 2 feet, and a height of 2 feet. In some embodiments, the apparatus is configured to fit within a box having a length of 3 feet, a width of 1 foot, and a height of 1 foot. In some embodiments, the apparatus is configured to fit within a box having a length of 2 feet, a width of 1 foot, and a height of 1 foot. In some embodiments, the apparatus is configured to fit within a box having a length of 1 foot, a width of 8 inches, and a height of 8 inches.

Some embodiments of the present methods of generating therapeutic shock waves, comprise: providing any of the present apparatuses; and actuating the apparatus to generate one or more shock waves. Some embodiments, further comprise: disposing the apparatus adjacent tissue of a patient such that at least one shock wave enters the tissue. In some embodiments, the tissue comprises skin tissue on the face of the patient.

Some embodiments of the present methods of generating therapeutic shock waves, comprise: actuating an acoustic-wave generator to emit acoustic waves having at least one frequency between 1 MHz and 1000 MHz, such that at least some portion of the acoustic waves travel through a shockwave medium that is disposed in a shockwave housing to form one or more shock waves.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every FIGURE in which that structure appears. Identical reference numbers do not necessarily indicate an identical structure. Rather, the same reference number may be used to indicate a similar feature or a feature with similar functionality, as may non-identical reference numbers.

The FIGURE depicts one of the embodiments of the present apparatuses for generating therapeutic shock waves.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a lid that "comprises," "has," "includes" or "contains" one or more elements possesses those one or more elements, but is not limited to possessing only those elements. For example, in a lid that comprises a body and an inner member, the lid includes the specified elements but is not limited to having only those elements. For example, such a lid could also include a cover member.

Further, a device or structure that is configured in a certain way is configured in at least that way, but it can also be configured in other ways than those specifically described.

There are a number of considerations for generating therapeutic shock waves from acoustic waves. For example, a classical effect of nonlinear acoustics is that a plain sinusoidal acoustic wave propagating in a nonlinear medium typically transforms to a sawtooth wave with one shock per cycle. In the past, it has been demonstrated that exposure of cells to high-power ultrasonic radiation under conditions excluding thermal cavitation-induced degradation, was accompanied by structural modification of macromolecules, nuclei, and intracellular submicroscopic complexes (Burov, 2002). Upon exposure to a shockwave, acceleration of structures within a cell due to the impact front may be very large. At the same time, elasticity of biological structures exposed to such large gradients of pressure is often significantly reduced. Under these conditions, cellular structures may behave as low-compliance materials. As a result, even a seemingly insignificant deformation may cause cell destruction. In addition, rapidly changing mechanical loads applied to structures periodically at a high frequency can lead to fatigue failure (Burov, 2002).

Tissues may be modified with ultrasound waves by modification of macromolecules, membranes, nuclei and intracellular submicroscopic complexes. Progressive nonlinear distortion of the waveform can result in the formation of pressure impact fronts, or shock waves, that cause deformation and failure of cells and subcellular structures. More specifically, progressive nonlinear distortion of the wavelength can result in formation of impact fronts that periodically follow each other with the frequency f. It was described in (Burov, 2002) that the duration of the front may be much shorter than the period 1/f as shown in Equation (1):

$$t = \frac{b}{\epsilon}(2I\rho c)^{1/2} \tag{1}$$

where b is the effective viscosity; e is the nonlinear factor; and $\rho$ and c are the medium density and speed of sound, respectively. As a result of this shock wave with its short duration, acceleration of higher-density particles within the cellular structure exposed to the impact front is typically very large. At the same time, elasticity of lower-density biological structures making up the cell structure exposed to such a large gradient of pressure is significantly reduced, and generally act as low-compliance material. The mismatch between biological structures within the cell, and cells' ability to experience deformation when exposed to the impact front, leads to cellular destruction (Burov, 2002).

While a cell may oscillate as an integral unit when impacted by these pressure fronts, sharp gradients of mechanical stress can be generated inside the cell as a result of spatial heterogeneity parameters (i.e., density and shear elasticity modulus). (Burov, 2002) illustrated this by modeling the biological structure as two linked balls with masses $m_1$ and $m_2$ and the density ($\rho_0$) of the liquid oscillating around the balls with the speed $\mu_o(t)$ differ insignificantly from the densities of the balls (by $\rho_1$ and $\rho_2$ respectively). If only the resistance to potential flow is taken into account, the force applied to the link is calculated as shown in Equation (2):

$$F = \frac{2}{3}\frac{m_1 m_2}{m_1 + m_2}\frac{[\rho_1 - \rho_2]}{\rho_0}\mu_0(t) \tag{2}$$

For example, if the ball radius (R) is about 10 μm and the difference between the densities of the balls is 0.1 $\rho_0$, and results in a stress force, $F/(\pi R^2)m$ of $10^9$ dyne/cm$^2$. This according to Burov was substantially greater than the cell membrane breaking point.

Referring now to the drawings, shown therein and designated by the reference numeral 10 is one embodiment of the present apparatuses for generating therapeutic shock waves (e.g., high-frequency shock waves), such as, for example, that can be delivered to tissue of a patient (e.g., a human patient). In the embodiment shown, apparatus 10 comprises: an acoustic-wave generator 14, a shockwave housing 18 coupled to acoustic-wave generator 14, and a shockwave medium 22 disposed in shockwave housing 18. In the embodiment shown, acoustic-wave generator 14 is configured to emit acoustic waves having at least one frequency between 1 megahertz (MHz) and 1000 MHz (e.g., 1 MHz, 2 MHz, etc.) (and/or at least one wavelength corresponding to at least one frequency between 1 MHz and 1000 MHz, such as, for example, in the shockwave medium 22, or in a reference medium such as, for example, atmospheric air). In the embodiment shown, acoustic-wave generator 14 comprises an ultrasound head (e.g., a commercially available ultrasound head). In some embodiments, acoustic-wave generator 14 comprises ceramic and/or a piezoelectric acoustic element. Apparatus 10 is configured such that if acoustic-wave generator 14 emits acoustic waves then at least some portion of the acoustic waves will travel through shockwave medium 22 and form one or more shock waves (e.g., in or near shockwave housing 18). For example, shockwave housing 18 (and shockwave medium 22) can have a length large enough to allow the transformation of the acoustic waves into shock waves; and/or acoustic-wave generator 14 can be actuated to emit acoustic waves at sufficient amplitude and frequency to induce shockwave (or shockwave-type) formations in the shock chamber. By way of another example, the progressive nonlinear distortion of the wavelength of the acoustic waves in the shockwave medium 22 can result in the formation of pressure impact fronts, or shock waves, that can cause deformation and/or failure of cells (e.g., when the shock waves are applied at an intensity and for a period of time sufficient to affect tissue). In some embodiments, acoustic-wave generator 14 is configured to emit acoustic waves with beam radian power of between about, or substantially equal to 5 and 1000 Watts per square centimeter (W/cm2) (e.g., 100 to 500 W/cm2, 100 to 400 W/cm2). In some embodiments, apparatus 10 is configured to generate 100 or more shockwaves per minute (e.g., 200, 300, 400, 500, 1000, 2000, 5000, or more shock waves per minute).

Apparatus 10, for example, can be operated to predictably and/or consistently generate shock waves that can be delivered to tissue in proximity of apparatus 10, for example, to cause cellular damage to the tissue (e.g., for medical and/or aesthetic therapeutic uses. Some embodiments of apparatus 10 can be configured to provide or generate shock waves at an energy level sufficient to cause membrane-degradation damage of cells. For example, when targeted tissue is exposed to high-frequency shockwaves, sharp gradients of mechanical stress can be generated inside the cell as a result of spatial heterogeneity parameters (i.e., density and shear elasticity modulus).

In the embodiment shown, shockwave housing 18 defines a chamber 26, and shockwave medium (or media) 22 is disposed in chamber 26. Housing 18 can comprise, for example, polymer, plastic, silicone, metal, and/or any other suitable material. Shockwave medium 22 can comprise a material that exhibits or is able to experience nonlinearities in the presence of acoustic waves generated or emitted from acoustic-wave generator 14. These nonlinearities can be induced from the diffraction of the ultrasound waves from the wall of shockwave housing 18. Additionally or alternatively, nonlinearities may result from inhomogeneities induced by ultrasound waves traveling through shockwave medium (or media) 22. Furthermore, nonlinearities can result from inclusion of particles or bubbles in the media (i.e. gas bubbles, nanoparticles, etc.). In some embodiments, shockwave medium 22 comprises a fluid. In some embodiments, shockwave medium 22 comprises a gel. In some embodiments, shockwave medium 22 comprises a liquid. In some embodiments, shockwave medium 22 is configured such that in the presence of acoustic waves from acoustic-wave generator 14, shockwave medium 22 will exhibit nonlinear properties. In some embodiments, shockwave medium 22 comprises one or more of: water, glycerin, poly(ethylene glycol) (PEG), propylene glycol, silicone oil, alcohol, or a combination of two or more of these. In some embodiments, shockwave medium 22 comprises one or more of: bubbles (e.g., gas bubbles), solid particles, or a combination of bubbles and solid particles. Gas bubbles can be introduced into medium 22, for example, by the addition of a gas such as carbon dioxide, and/or can be introduced in the form of stabilized gas bubbles found in ultrasound contrast media or as part of nanoparticles.

Additionally, in the embodiment shown, shockwave housing 18 defines chamber 26 having an inlet end 30 coupled to acoustic-wave generator 14, and an outlet end 34 extending from acoustic-wave generator 14. Some embodiments of shockwave housing 18 can also include an end cap 38 covering outlet end 34 of chamber 26. In the embodiment shown, chamber 26 has a circular cross-sectional shape. In other embodiments, chamber 26 has a rectangular, square, ovular, triangular, octagonal, and/or any other suitable cross-sectional shape. In some embodiments, shockwave housing 18 is configured such that distance 42 from acoustic-wave generator 14 (e.g., at inlet end 30 of chamber 26) to outlet end 38 of chamber 26 is between 100 and 1000 percent of at least one (e.g., the minimum) internal transverse dimension (e.g., diameter 42) of chamber 26. In some embodiments, distance 46 from acoustic-wave generator 14 (e.g., at inlet end 30 of chamber 26) to outlet end 34 of chamber 26 is between 300 and 900 percent (and/or between 400 and 800 percent) of at least one (e.g., the minimum) internal transverse dimension (e.g., diameter 42) of the chamber.

In some embodiments, inlet end 30 of chamber 26 has a transverse internal dimension (e.g., diameter 42) at least as large as a corresponding transverse external dimension of acoustic-wave generator 14 (e.g., at output end 50). For example, in the embodiment shown, diameter 42 of chamber 26 is at least as large as (e.g., just larger than) the outer diameter of a corresponding portion (e.g., output end 50) of acoustic-wave generator 14. In other diameters, diameter 42 can be larger (e.g., and/or a gasket or coupler can be used to couple housing 18 to output end 50 of acoustic-wave generator). In the embodiment shown, chamber 26 has a substantially constant cross-section between inlet end 30 and outlet end 34. In other embodiments, chamber 26 has a varying cross-section between inlet end 30 and outlet end 34.

In some embodiments, a suitable length 46 of shockwave chamber 26 is a function of a nonlinear parameter, pressure amplitude, frequency of the ultrasound wave, the density of medium 22, and the speed of sound in medium 22. For example, distance 46 from acoustic-wave generator 14 (e.g., at inlet end 30 of chamber 26) to outlet end 34 of chamber 26 may be greater than or equal to that given by Equation (3):

$$L = \frac{c_0^3 \rho_0}{\epsilon \omega P_0} = \frac{\lambda}{2\pi M_\omega} \qquad (3)$$

where $\epsilon$ =nonlinear parameter of shockwave medium; $\omega$=frequency of acoustic wave; $\rho_0$=density of the shockwave medium; $\lambda$=wavelength of acoustic wave; $c_0$=velocity of sound in the shockwave medium; $P_0$=pressure amplitude in shockwave medium; and $M_\omega$=acoustic mach number=$P_0 \div (c_0^2 \rho_0)$. In general, the higher the frequency and/or the higher the intensity, the shorter length 46 of chamber 26 must be to permit shock wave formation at or before outlet end 34 (and/or before end cap 38) of chamber 26.

Additionally, in the embodiment shown, shockwave housing 18 is configured such that if acoustic waves are incident on shockwave housing 18 from within shockwave chamber 26, then shockwave housing 18 will reflect at least some portion of the incident acoustic waves back into shockwave chamber 26.

In the embodiment shown, end cap 38 is configured enclose outlet end 34 of chamber 26 such that medium 22 is substantially prevented from exiting chamber 26, and to permit shockwaves to exit outlet end 34 of shockwave chamber 26. In some embodiments, end cap 38 is configured to have a low shockwave attenuation (e.g., such that attenuation of a shockwave exiting end cap 38 will be less than twenty percent) and/or low shockwave reflection. In some embodiments, end cap 38 comprises at least one of: polymer, hydrogel, membrane, plastic, or silicone.

In other embodiments, shockwave medium 22 is unitary with shockwave housing 18 (e.g. comprise the same piece of material. In some embodiments, shockwave housing 18 and shockwave medium 22 comprise silicone. In other embodiments, shockwave medium 22 comprises one or more bubbles (e.g., gas bubbles or the like).

In the embodiment shown, apparatus 10 further comprises: a controller 54 coupled to acoustic-wave generator 14 and configured to actuate acoustic-wave generator 14 to emit acoustic waves. Controller 54 can comprise any suitably programmed hardware, such as, for example, a processor with memory, a programmable logic controller (PLC), and a personal digital assistant (PDA), and/or the like. Although illustrated as a separate component, controller 54 can be integrated into (e.g., share a common housing with) acoustic-wave generator 14. In some embodiments, controller 54 is configured to adjust acoustic-wave generator 14 to vary at least one of the amplitude and frequency of acoustic waves emitted from acoustic-wave generator 14. In some embodiments, controller 54 is configured to actuate acoustic-wave generator 14 to continuously emit acoustic waves for a period of time (e.g., when acoustic-wave generator is actuated to be 'on'). In some embodiments, controller 54 is configured to actuate acoustic-wave generator 14 to emit acoustic waves in a periodic on-off sequence (e.g., a sequence with regular, periodic intervals). In some embodiments, controller 54 is configured to actuate acoustic-wave generator 14 to emit acoustic waves in an intermittent on-off sequence (e.g., a non-periodic sequence without regular, periodic intervals). Actuation of acoustic-wave generator 14 in an on-off sequence can, for example, reduce heat buildup in tissue. In some embodiments, controller 54 is configured to actuate acoustic-wave generator 14 to emit acoustic waves in an on-off sequence, and to adjust the duration of "on" and/or "off" portions of the on-off sequence based on or responsive to measured and/or predicted temperature. For example, temperature can be measured with a thermometer (e.g., infrared thermometer) coupled to controller 54, and/or controller 54 can be configured to predict tissue temperature based, at least in-part, on intensity and/or other properties of acoustic waves emitted from acoustic-wave generator 14 and/or shock waves generated in housing 18 or delivered to tissue.

In some embodiments, acoustic-wave generator 14 is a first acoustic-wave generator, and apparatus 10 further comprises: a second acoustic-wave generator (not shown) configured to emit acoustic waves having at least one frequency between 1 MHz and 1000 MHz; where shockwave housing 18 is also coupled to the second acoustic-wave generator. In such embodiments apparatus 10 is configured such that if the second acoustic-wave generator emits acoustic waves then at least some portion of the acoustic waves will travel through shockwave medium or media 22 and form one or more shock waves. Some of these embodiments further comprise a controller 54 coupled to the second acoustic-wave generator and configured to actuate second the acoustic-wave generator to emit acoustic waves. In some embodiments, controller 54 is configured to actuate first acoustic-wave generator 14 and the second acoustic-wave generator (not shown) such that the acoustic waves that are emitted from the second acoustic-wave generator are out-of-phase from the waves that are emitted from first acoustic-wave generator 14.

In some embodiments, apparatus 10 is configured to fit within a box having a length of 3 feet, a width of 2 feet, and a height of 2 feet. In some embodiments, apparatus 10 is configured to fit within a box having a length of 3 feet, a width of 1 foot, and a height of 1 foot. In some embodiments, apparatus 10 is configured to fit within a box having a length of 2 feet, a width of 1 foot, and a height of 1 foot. In some embodiments, apparatus 10 is configured to fit within a box having a length of 1 feet, a width of 8 inches, and a height of 8 inches.

Embodiments of the present apparatuses (e.g., apparatus 10) can be used for wrinkle reduction. For example, some embodiments of the present methods of generating therapeutic shock waves, comprise: providing any of the present apparatuses (e.g., apparatus 10); and actuating the apparatus to generate one or more shock waves. Some embodiments further comprise: disposing the apparatus (e.g., outlet end 34 of housing 18) adjacent tissue of a patient such that at least one shock wave enters the tissue. In some embodiments, the tissue comprises skin tissue on the face of the patient.

Some embodiment of the present methods of generating therapeutic shock waves, comprise: actuating an acoustic-wave generator (e.g., 14) to emit acoustic waves having at least one frequency between 1 MHz and 1000 MHz, such that at least some portion of the acoustic waves travel through a shockwave medium (e.g., 22) that is disposed in a shockwave housing (e.g., 18) to form one or more shock waves.

The various illustrative embodiments of devices, systems, and methods described herein are not intended to be limited to the particular forms disclosed. Rather, they include all modifications and alternatives falling within the scope of the claims. For example, the present watering systems can include any number of basins in any of the shapes that are described and/or depicted.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus for generating therapeutic shock waves, comprising:
    an acoustic-wave generator configured to emit unfocused sinusoidal acoustic waves having at least one frequency between 1 MHz and 1000 MHz;
    a shockwave housing coupled to the acoustic-wave generator; and
    a shockwave medium disposed in and contained by the shockwave housing, said shockwave medium is configured to exhibit nonlinear properties in the presence of at least one emitted acoustic wave;
    where the apparatus is configured to propagate at least a portion of the emitted acoustic waves through the shockwave medium to form one or more unfocused shock waves that exit a distal end of the shockwave housing and rupture at least one cellular structure.

2. The apparatus of claim 1, where the shockwave medium occupies all of a cavity defined by the shockwave housing.

3. The apparatus of claim 1, where the shockwave medium comprises at least one of: polymer, hydrogel, silicone, metal, or any combination thereof.

4. The apparatus of claim 1, where the shockwave housing defines a chamber having an inlet end coupled to the acoustic-wave generator and an outlet end extending from the acoustic-wave generator, and where the shockwave housing includes an end cap covering the outlet end of the chamber.

5. The apparatus of claim 4, where the end cap is configured such that attenuation of a shockwave exiting the end cap will be less than twenty percent.

6. The apparatus of claim 4, where the shockwave housing is configured such that if acoustic waves are incident on the shockwave housing from within the chamber, then the shockwave housing will reflect at least a portion of the incident acoustic waves back into the chamber.

7. The apparatus of claim 1, where the length of the shockwave medium is greater than or equal to the value of L determined by a first equation:

$$L = \frac{c_0^3 \rho_0}{\epsilon \omega P_0} = \frac{\lambda}{2\pi M_\omega};$$

where $\epsilon$=nonlinear parameter of shockwave medium; $\omega$=frequency of an acoustic wave the acoustic-wave generator is configured to emit; $\rho_0$=density of the shockwave medium; $\gamma$=wavelength of the acoustic wave; $c_0$=velocity of sound in the shockwave medium; $P_0$=pressure amplitude in shockwave medium; and $M_\omega$=acoustic mach number=$P_0 \div (c_0^2 \rho_0)$.

8. The apparatus of claim 7 wherein the length of the shockwave medium is greater than the value L of the first equation but shorter than an attenuation length of the shockwave medium.

9. The apparatus of claim 7 wherein the length of the shockwave medium is shorter than an attenuation length of the shockwave medium.

10. The apparatus of claim 1, where the acoustic-wave generator comprises an ultrasound head.

11. The apparatus of claim 1, further comprising:
a controller coupled to the acoustic-wave generator and configured to actuate the acoustic-wave generator to emit the sinusoidal acoustic waves.

12. The apparatus of claim 11, where the controller is configured to adjust the acoustic-wave generator to vary at least one of the amplitude and frequency of the sinusoidal acoustic waves emitted from the acoustic-wave generator.

13. The apparatus of claim 11, where the controller is configured to actuate the acoustic-wave generator to continuously emit the sinusoidal acoustic waves.

14. The apparatus of claim 11, where the controller is configured to actuate the acoustic-wave generator to emit the sinusoidal acoustic waves in an intermittent on-off sequence.

15. The apparatus of claim 11, where the controller is configured to actuate the acoustic-wave generator to emit the sinusoidal acoustic waves in a periodic on-off sequence.

16. The apparatus of claim 1, where the acoustic-wave generator is configured to generate shock waves having an intensity between 50 and 1000 Watts per square centimeter (W/cm2).

17. The apparatus claim 1, where the acoustic-wave generator is configured to enable generation of at least 100 shockwaves per minute.

18. The apparatus of claim 1, where the apparatus is configured to fit within a box having a length of 3 feet, a width of 2 feet, and a height of 2 feet.

19. The apparatus of claim 1 wherein at least a portion of the one or more unfocused shock waves is formed in the shockwave medium.

20. A method of generating therapeutic shock waves, comprising:
providing a plurality of unfocused sinusoidal acoustic waves having at least one frequency of at least 1 MHz;
propagating at least a portion of the unfocused acoustic waves through a shockwave medium disposed in and contained by a shockwave housing, the shockwave medium configured to exhibit nonlinear properties in the presence of the propagated unfocused acoustic waves; and
generating one or more unfocused shock waves from said propagation of at least the portion of the unfocused acoustic waves through the shockwave medium such that the shock waves exit a distal end of the shockwave housing; and
rupturing at least one cellular structure by delivery of the one or more unfocused shock waves.

21. The method of claim 20 further comprising the step of varying the frequency of the acoustic waves.

22. The method of claim 20 further comprising the step of varying the amplitude of the acoustic waves.

23. The method of claim 20 wherein the one or more unfocused shock waves are generated in said shockwave medium.

24. The method of claim 20 further comprising the step of actuating a first acoustic wave generator to provide the plurality of unfocused acoustic waves.

* * * * *